United States Patent
Collier et al.

(10) Patent No.: US 10,406,014 B2
(45) Date of Patent: Sep. 10, 2019

(54) LOW-PROFILE, POSTURAL CORRECTIVE GARMENT FOR THERAPEUTIC RELIEF OF LOW BACK PAIN AND MECHANICAL LUMBAR DISORDERS

(71) Applicant: ActivAided Orthotics LLC, Pittsburgh, PA (US)

(72) Inventors: Kelly N. Collier, West Mifflin, PA (US); Gary P. Chimes, Redmond, WA (US); Brianne Burton, Amherst, NY (US); Alice Mayfield, Wheat Ridge, CO (US); Philip Manor, Niskayuna, NY (US); Divya Krishnamoorthy, Shelton, CT (US)

(73) Assignee: Advanced Integration Motion, LLC, Pittsburgh, PA (US)

( * ) Notice: Subject to any disclaimer, the term of this patent is extended or adjusted under 35 U.S.C. 154(b) by 731 days.

(21) Appl. No.: 14/383,788

(22) PCT Filed: Mar. 13, 2013

(86) PCT No.: PCT/US2013/030885
§ 371 (c)(1),
(2) Date: Sep. 8, 2014

(87) PCT Pub. No.: WO2013/138468
PCT Pub. Date: Sep. 19, 2013

(65) Prior Publication Data
US 2015/0148727 A1    May 28, 2015

Related U.S. Application Data

(60) Provisional application No. 61/610,005, filed on Mar. 13, 2012.

(51) Int. Cl.
*A61F 5/03* (2006.01)
*A61F 5/02* (2006.01)

(52) U.S. Cl.
CPC ............ *A61F 5/026* (2013.01); *A61F 5/03* (2013.01)

(58) Field of Classification Search
CPC .. A61F 5/024; A61F 5/026; A61F 5/02; A61F 5/022; A41D 13/0007
(Continued)

(56) References Cited

U.S. PATENT DOCUMENTS 766,863 A * 8/1904 Adams .................... A61F 5/026
602/19
3,292,616 A * 12/1966 Freeman .................. A61F 5/03
450/96

(Continued)

FOREIGN PATENT DOCUMENTS

WO    2008/137810 A1    11/2008

OTHER PUBLICATIONS

International Search Report and Written Opinion of the International Searching Authority for PCT Application PCT/US2013/030885 dated Jun. 21, 2013.

*Primary Examiner* — Kari Rodriquez
*Assistant Examiner* — Camtu Nguyen
(74) *Attorney, Agent, or Firm* — David G. Oberdick

(57) ABSTRACT

Postural corrective device including a flexible back support system incorporated into a body suit that trains self-corrective habits through proprioceptive feedback, offering gentle reminders to create awareness of what the wearer's body is doing.

11 Claims, 21 Drawing Sheets

(58) Field of Classification Search
USPC .............. 2/44–45, 461, 464, 467; 128/96.1
See application file for complete search history.

(56) References Cited

U.S. PATENT DOCUMENTS

| | | | | |
|---|---|---|---|---|
| 3,338,236 | A * | 8/1967 | McLeod, Jr. | ....... A61F 5/05808 128/DIG. 19 |
| 3,897,776 | A * | 8/1975 | Gaylord, Jr. | ........ A61F 5/05808 128/DIG. 19 |
| 4,802,469 | A | 2/1989 | Gollestani | |
| 5,135,470 | A * | 8/1992 | Reeves | ................... A61F 5/026 2/44 |
| 5,205,815 | A * | 4/1993 | Saunders | ........... A41D 13/0525 450/150 |
| D429,384 | S | 8/2000 | Crupi et al. | |
| 6,119,275 | A * | 9/2000 | Goyal | .................... A41B 9/001 2/228 |
| 6,190,342 | B1 * | 2/2001 | Taylor | .................... A61F 5/026 602/19 |
| 6,755,799 | B2 | 6/2004 | Toda | |
| 6,766,532 | B1 | 7/2004 | Cabana | |
| 6,962,572 | B1 | 11/2005 | Zahiri | |
| 7,001,350 | B2 | 2/2006 | Grosso | |
| D595,480 | S | 7/2009 | Giugliano | |
| 7,662,121 | B2 | 2/2010 | Zours | |
| 7,871,388 | B2 * | 1/2011 | Brown | .................... A61F 5/026 602/19 |
| 7,878,996 | B2 | 2/2011 | Smith | |
| 2008/0125842 | A1 | 5/2008 | Petitt | |
| 2009/0062704 | A1 | 5/2009 | Brown et al. | |
| 2010/0010568 | A1 | 1/2010 | Brown | |
| 2010/0256717 | A1 | 10/2010 | Brown | |
| 2012/0059297 | A1 * | 3/2012 | Newkirk | ................. A61F 5/028 602/19 |
| 2012/0078147 | A1 | 3/2012 | Ogulnick | |

* cited by examiner

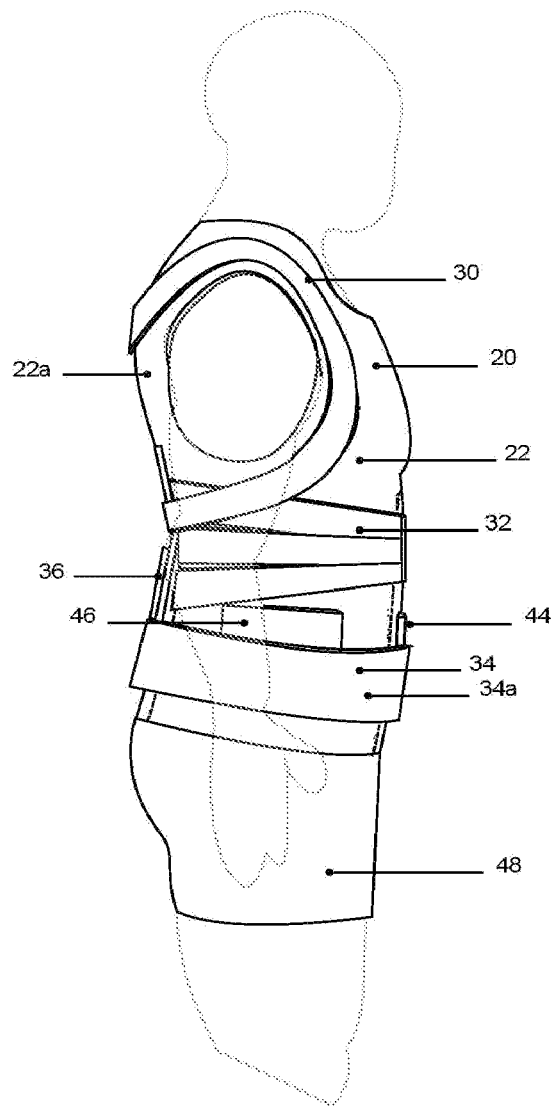
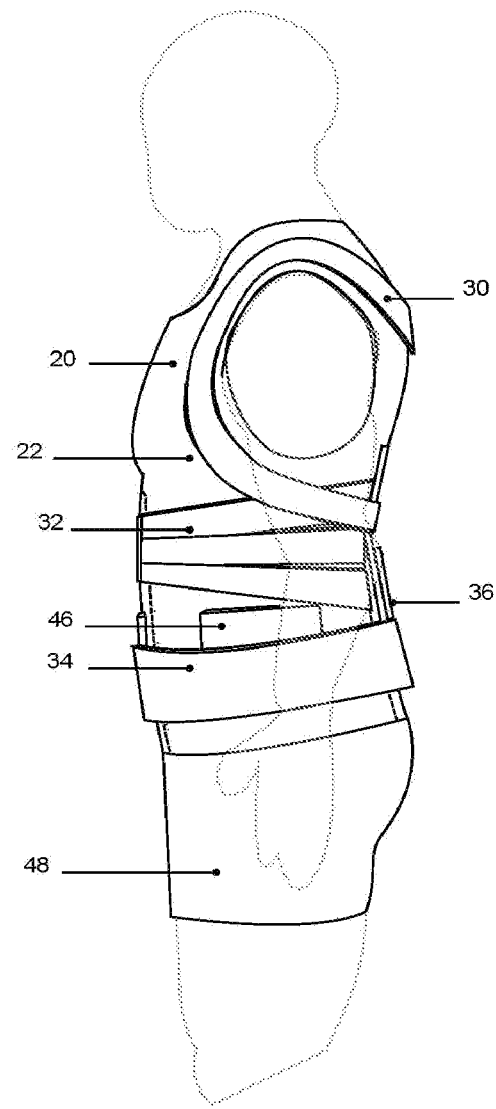
Figure 13
Figure 14

LOW-PROFILE, POSTURAL CORRECTIVE GARMENT FOR THERAPEUTIC RELIEF OF LOW BACK PAIN AND MECHANICAL LUMBAR DISORDERS

CROSS REFERENCE TO RELATED APPLICATIONS

The application of a 35 U.S.C. 371 U.S. national phase application of PCT international application s/n PCT/US2013/030885, filed on Mar. 13, 2013, which claims priority to U.S. Provisional Application Ser. No. 61/610,005, filed on Mar. 13, 2012, both of which are herein incorporated by reference in its entirety.

FIELD OF THE INVENTION

The present invention relates to flexible back support systems incorporated into garments that train self-corrective habits through proprioceptive feedback.

BACKGROUND OF THE INVENTION

Good posture is important to overall health. Good posture, or neutral spine, is the natural curve present in a healthy spine. The natural curve will include a slight forward curve in the lumbar (lower back) region, and a slight backward curve in the thoracic (upper back) region. When the back is in this position, the ears, shoulders, hips, knees, and ankles are aligned. This alignment properly distributes body weight and the stresses it causes along the length of the spine.

When a person has bad posture they are susceptible to several health risks including headaches, diminished breathing, and back pain. Musculoskeletal injuries can also occur from the abnormal distribution of stresses created by bad posture. This leads to structural changes in the spine including deterioration of discs and joints, wear and tear of cartilage, and lengthening or shortening supportive ligaments and muscles. Persons who spend most of their day sitting can be at an increased risk if they sit with poor posture, especially drivers and those who work at computers. Back pain can also lead to psychological distress.

Pro-longed poor posture can begin to feel normal and eventually lead to even worse posture, further injuring the back in a vicious cycle. Poor posture that feels normal can be very difficult to correct because the person's muscle memory for correct posture has been replaced with muscle memory for poor posture, and therefore correct posture feels incorrect. Conscious attempts at correcting posture are difficult because the distractions of daily life may prevent the proper amount of awareness of spinal positioning.

There are many treatments for the negative effects of poor posture. Some techniques include exercise, manual manipulation such as chiropractic care, and cutaneous stimulation. Drugs may also be utilized, such as pain relievers and muscle relaxants. Invasive techniques including back surgery are also used in extreme situations.

Some medical devices have also been developed to avoid these problems. Hard immobile back braces are common for those with extreme spine misalignment are not comfortable and interfere with mobility. Other devices provide support to only a section of the spine, can be bulky, and often restrict mobility. Still others mechanically manipulate the body into correct posture in ways that can be uncomfortable to the wearer. Still others address pain in the back but without treating the underlying cause such as thermotherapy.

There exists a need in the art for a system that trains a user to use correct posture for the entire spine, the neutral position, to prevent the back problems caused by poor posture. There further exists a need for a system that accomplishes that comfortably and subtly without unduly restricting motion so as not to interfere with the user's daily life. There further exists a need for a system that relieves the pain associated with poor posture while training proper posture.

SUMMARY OF THE INVENTION

The present invention is a postural corrective device that includes a flexible back support system incorporated into a garment. It trains self-corrective habits through proprioceptive feedback, offering gentle reminders to create awareness of what the wearer's body is doing. The garment can include shorts to anchor the shirt portion of the garment. The body suit does not mechanically manipulate the wearer's body; rather it encourages the user to use her/his body in such a way to reverse the damage that has been done to the tissues in the lower back over a period of time. Spine stabilization, the key to back pain relief and injury prevention, is achieved by promoting proper motion patterns and distributing force evenly throughout the entire back. This is accomplished through posture control, core conditioning, neutral spine positioning, and temporary pain relief resulting from supplying intervertebral pressure and compression, while also facilitating mobility.

BRIEF DESCRIPTION OF THE DRAWINGS

FIG. 13 is a right side view of the postural corrective garment of another embodiment where all detachable and removable optional components are included;

FIG. 14 is a left side view of the postural corrective garment of another embodiment where all detachable and removable optional components are included;

DETAILED DESCRIPTION OF THE INVENTION

Figure 24:
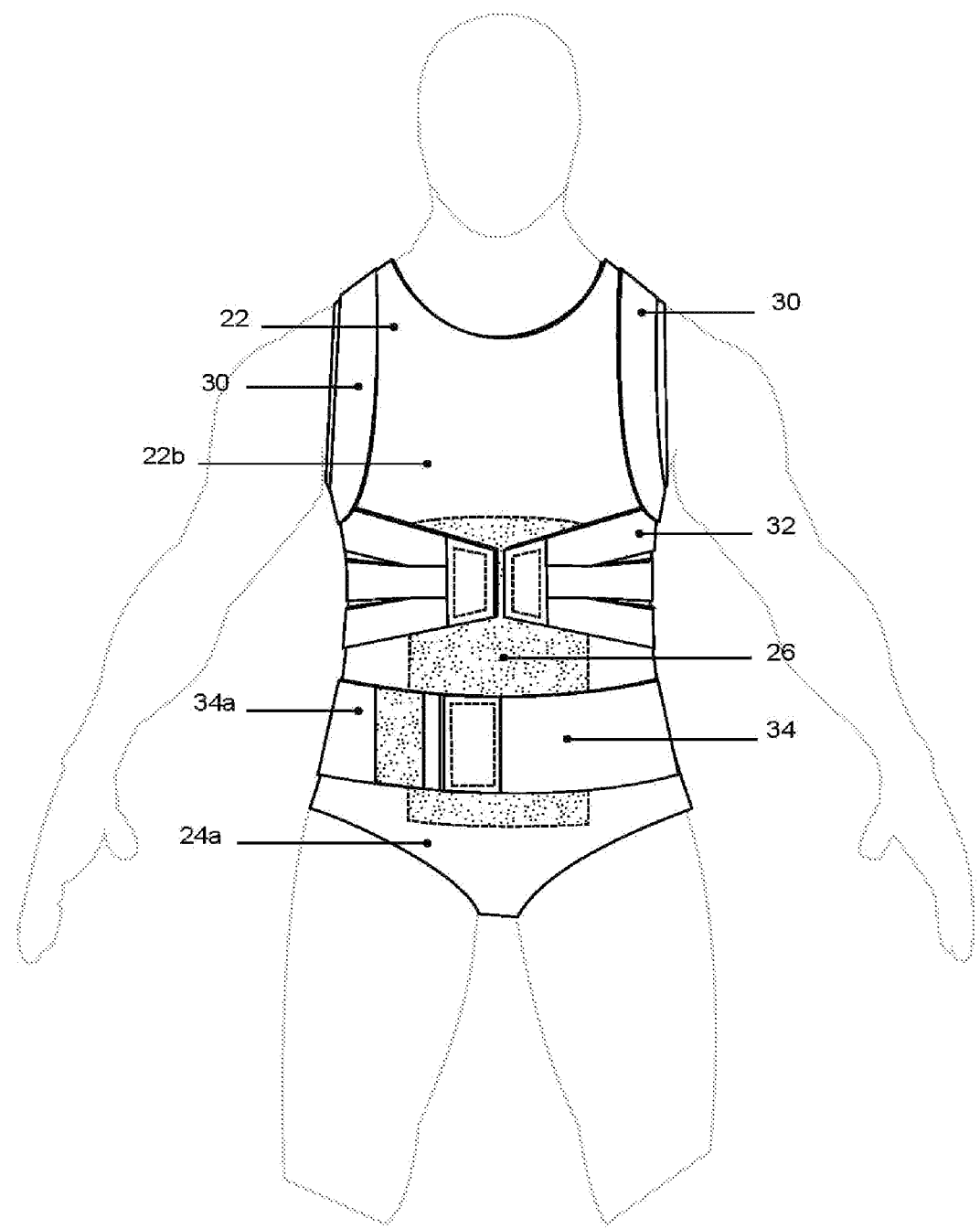
FIG. 24 is a front view of an alternative embodiment where the postural corrective device is built as a body suit.

Referring now to the drawings to illustrate an exemplary embodiment of the present invention 20, but not for the purpose of limiting the scope of the invention in any way, FIGS. 1-6 provide back, front, right, left, top and bottom views, respectively, of one embodiment of the postural corrective device 20 including a garment which can have two pieces, a shirt portion 22 and a shorts portion 48, connected to form a body suit 24. In this embodiment, the shirt portion 22 includes a back panel 28 and a front panel 26, and these panels are made of non-stretch material to provide structural support to the shirt portion 22 when tension is applied. These front and back panels 26, 28 are also made of loop material which is conducive to a cooperating hook and loop attachment system. In other embodiments, these panels 26, 28, individually or collectively, may be optional. Similarly, in another embodiment, the postural corrective device 20, including the shirt portion 22 and the shorts portion 48, may be sewn as one continuous piece of clothing including shirt portion 22 and shorts portion 48 to form a body suit 24—similar to a leotard style of clothing as demonstrated in FIG. 24, or the shorts portion 48 may be omitted from the postural corrective device 20 leaving only the shirt portion 22.

Figure 1:
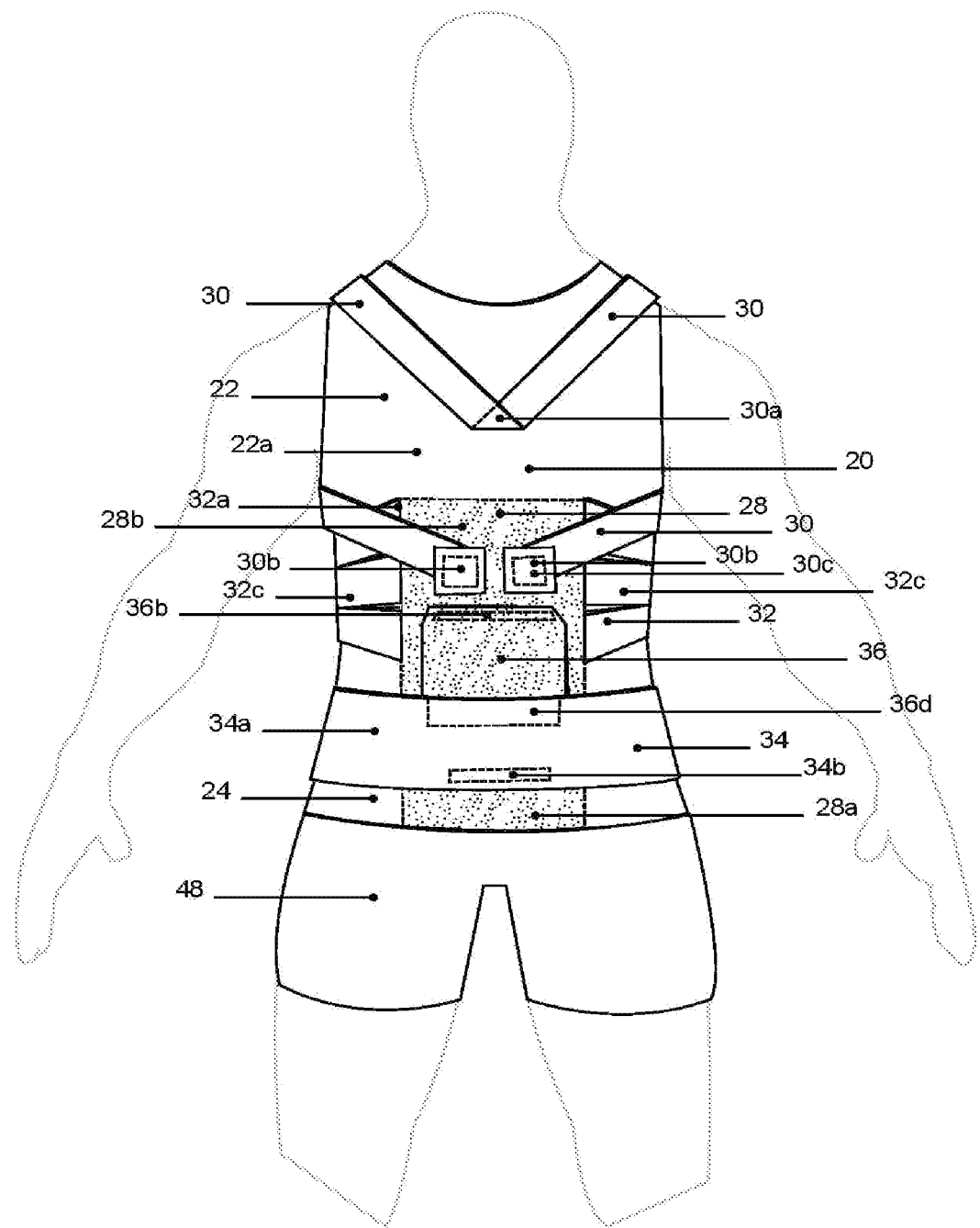
FIG. 1 is a back view of the postural corrective garment of an exemplary embodiment.

Now turning to FIG. 1 illustrating a back view of the postural corrective device 20 of an exemplary embodiment with other aspects of the invention attached to the loops 28a of the exposed side 28b of the back panel 28, and showing the relative positioning of the back panel on the shirt portion 22. The back panel 28 can be a patch of non-stretch material covering the middle and lower back of the wearer or integrated into the shirt portion 22. The exposed side 28b of the back panel 28 can include loops 28a in an adjustable hook and loop fastening system. Other adjustable fastening systems can also be used.

Figure 2:
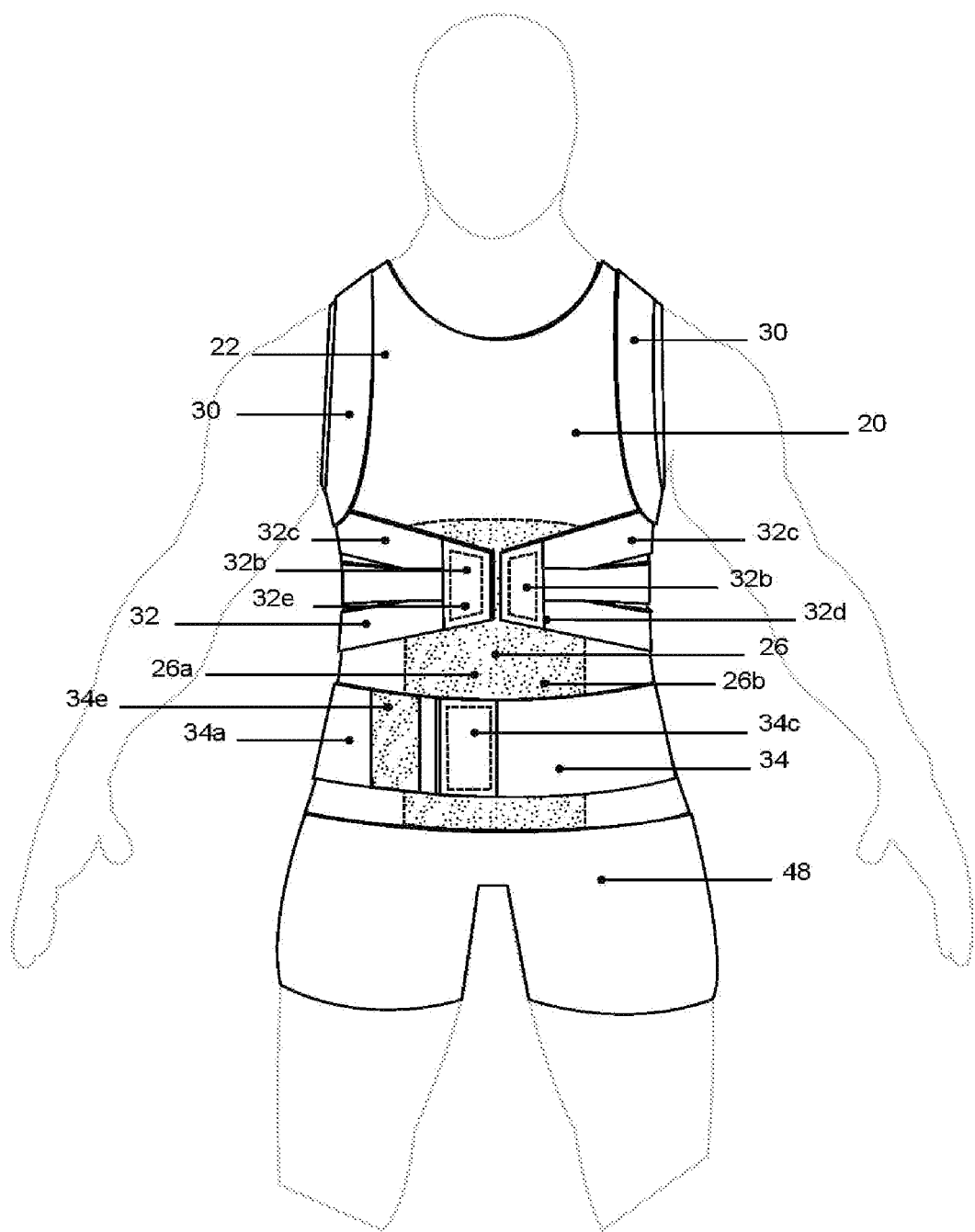
FIG. 2 is a front view of the postural corrective garment of an exemplary embodiment.

Now turning to FIG. 2 illustrating a front view of the postural corrective device 20 and shows the front panel 26 of the shirt portion 22 of an exemplary embodiment with other aspects of the invention attached to the loops 26a of the exposed side 26b of the front panel 26. The front panel 26 can be a patch of non-stretch material covering the rectus abdominis of the wearer or integrated into the shirt portion 22. The exposed side 26b of the front panel 26 can include loops 26a in an adjustable hook and loop fastening system. Other adjustable fastening systems can also be used. In comparison, FIG. 7 is a front view of the postural corrective device 20 and shows the front panel 26 of the shirt portion 22 of an exemplary embodiment with its loops 26a free from any hook attachments.

Figure 8A:
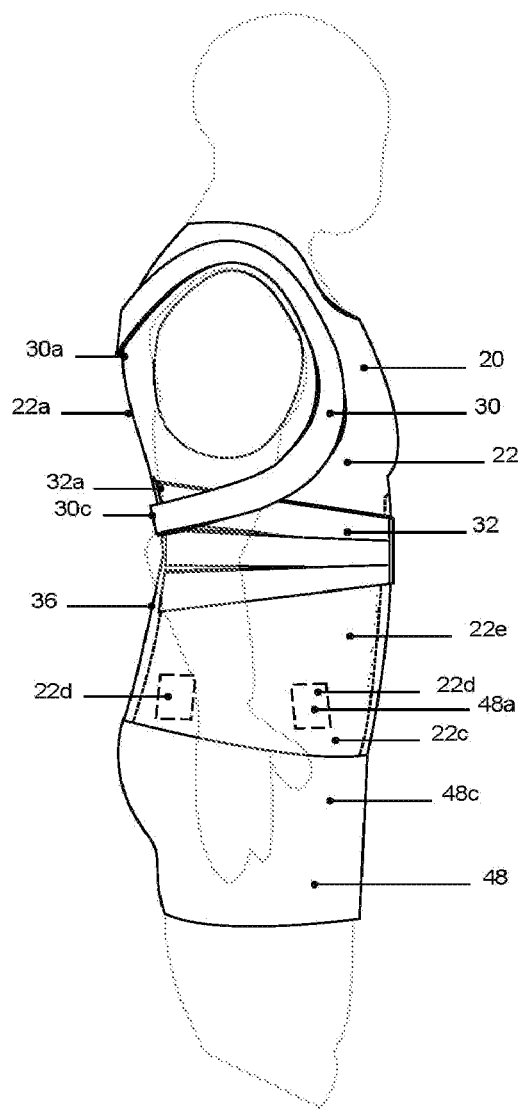
FIGS. 8A and 8B are right and left side views, respectively, where 8B is of the postural corrective garment with the shirt portion removed so that the shorts portion, including a hook and loop closure, is entirely visible; 8A shows the shirt portion connected to the outer surface of the shorts portion with the hook and loop closure.
Figure 8B:
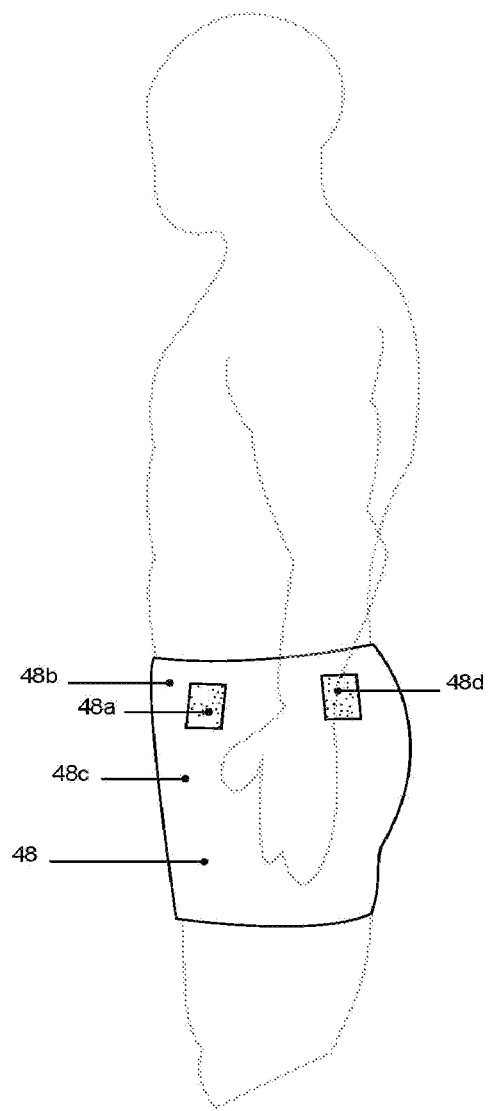
Figures 25A, 25B:
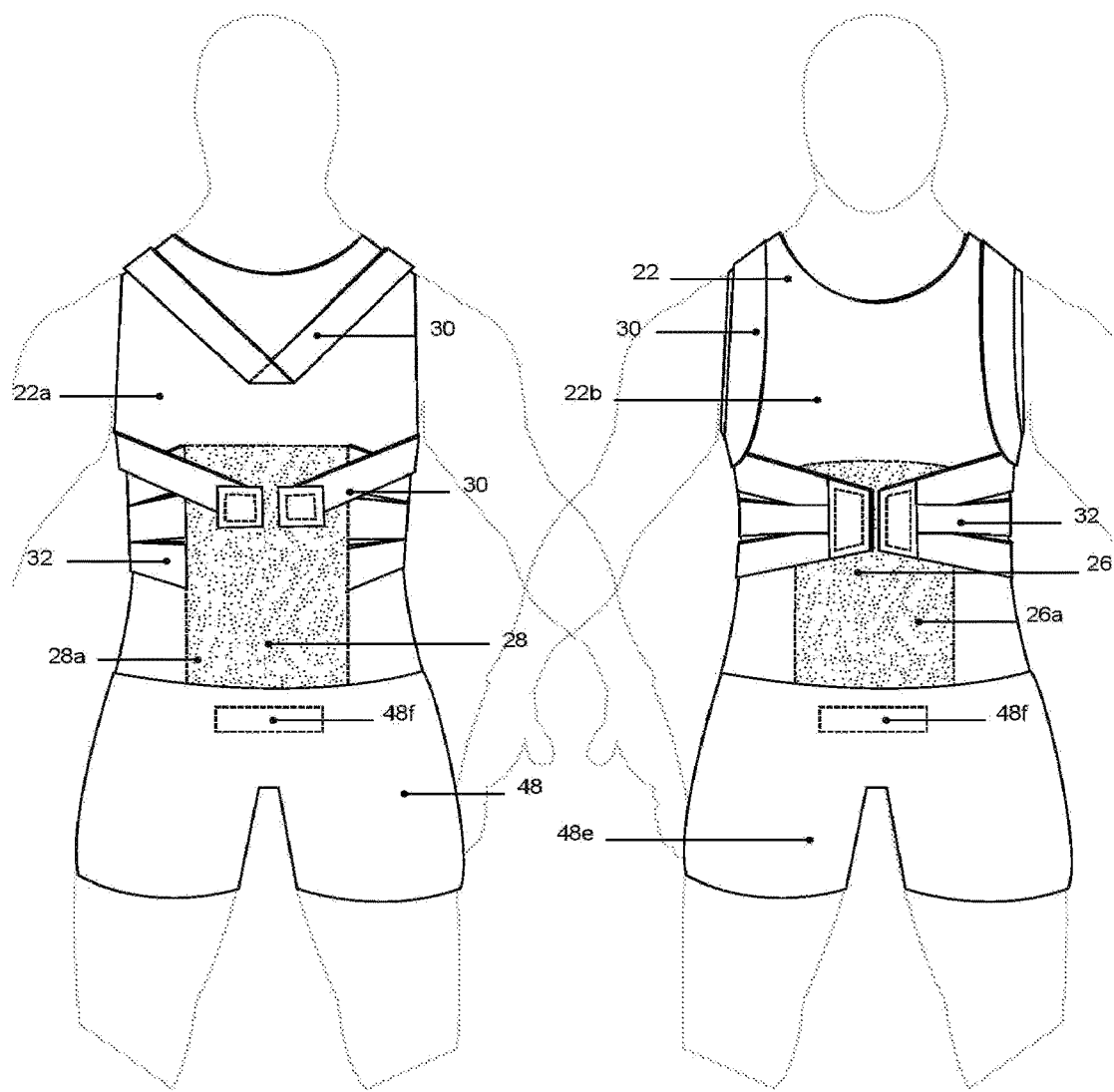
FIGS. 25A and 25B are back and front views, respectively, of the postural corrective garment of an exemplary embodiment where the shorts portion is connected with a hook and loop closure to the outer surface of the shirt portion.

Now turning to FIG. 8B, the shorts portion 48 contains sections of a hook and loop fastening system 48d on the outer surface 48c of the shorts portion 48 along the top 48b which corresponds to a hook and loop fastening system on the inner surface 22d along bottom 22c (see FIG. 8A) of the shirt portion 22. FIG. 8B shows a left side view of the postural corrective device 20 of an exemplary embodiment with the shirt portion 22 removed, such that the hook and loop material 48d on the outer surface 48c of shorts portion 48 is visible. FIG. 8A shows a right side view where the shirt portion 22 has been added to fit over the top 48b of the shorts portion 48 and the corresponding hook and loop materials 22d on the inner surface of the shirt portion 22 along bottom 22c and hook and loop materials 48d of the shorts portion 48 may be attached. As shown in FIGS. 25A and 25B, the shorts portion 48 may also attach overtop of the shirt portion 22, where the shorts portion hook and loop materials are attached to the front 26a and back 28a outer surface of the shirt portion 22e along the bottom 22c. In this embodiment, the shorts portion 48 hook and loop materials 48d are attached to the inner surface 48f of the shorts portion 48 along top 48b.

Figure 3:
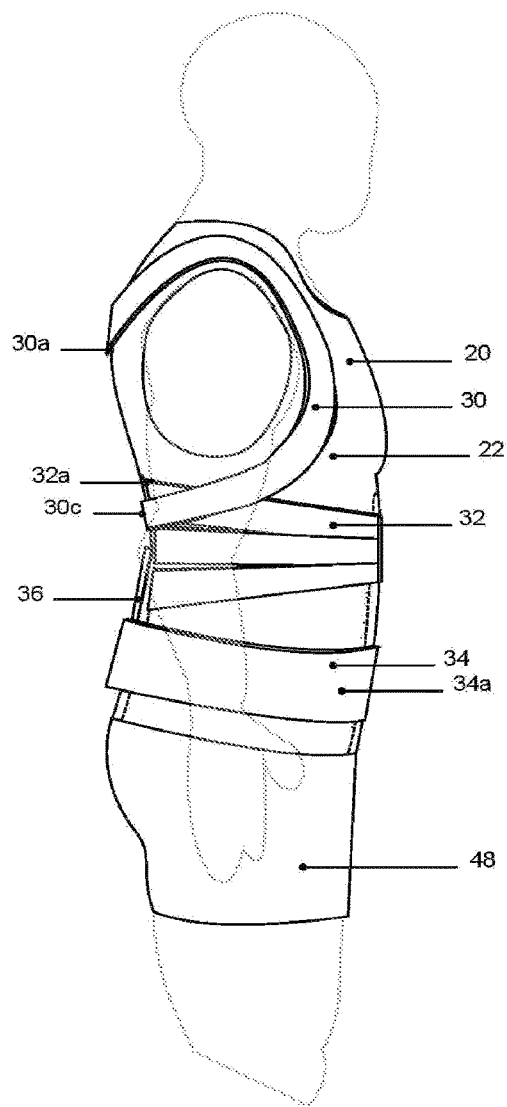
FIG. 3 is a right side view of the postural corrective garment of an exemplary embodiment.
Figure 4:
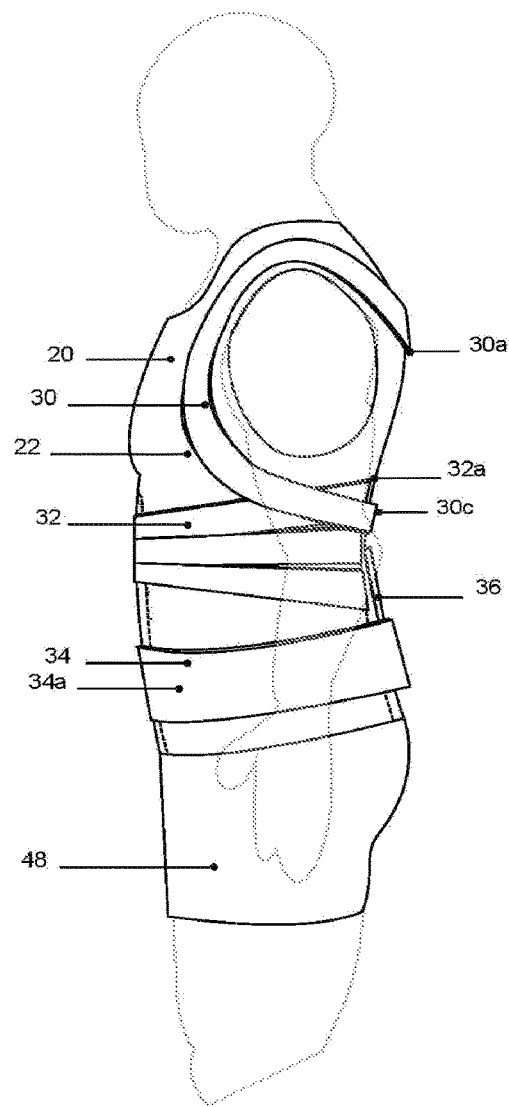
FIG. 4 is a left side view of the postural corrective garment of an exemplary embodiment.
Figure 5:
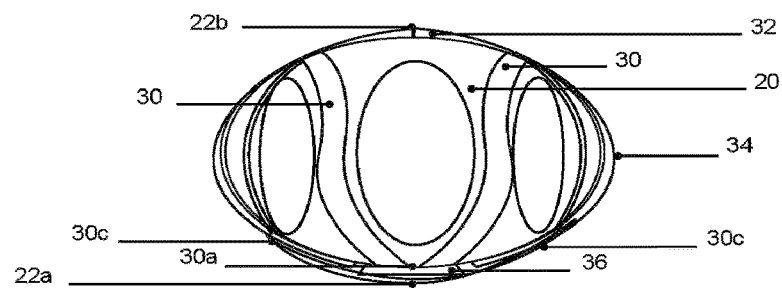
FIG. 5 is a top view of the postural corrective garment of an exemplary embodiment.
Figure 6:
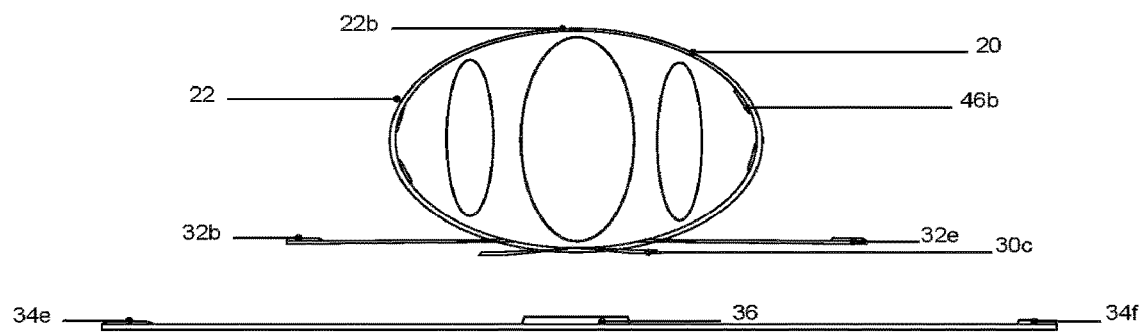
FIG. 6 is a bottom view of the postural corrective garment of an exemplary embodiment, where all detachable components are disengaged.
Figure 7:
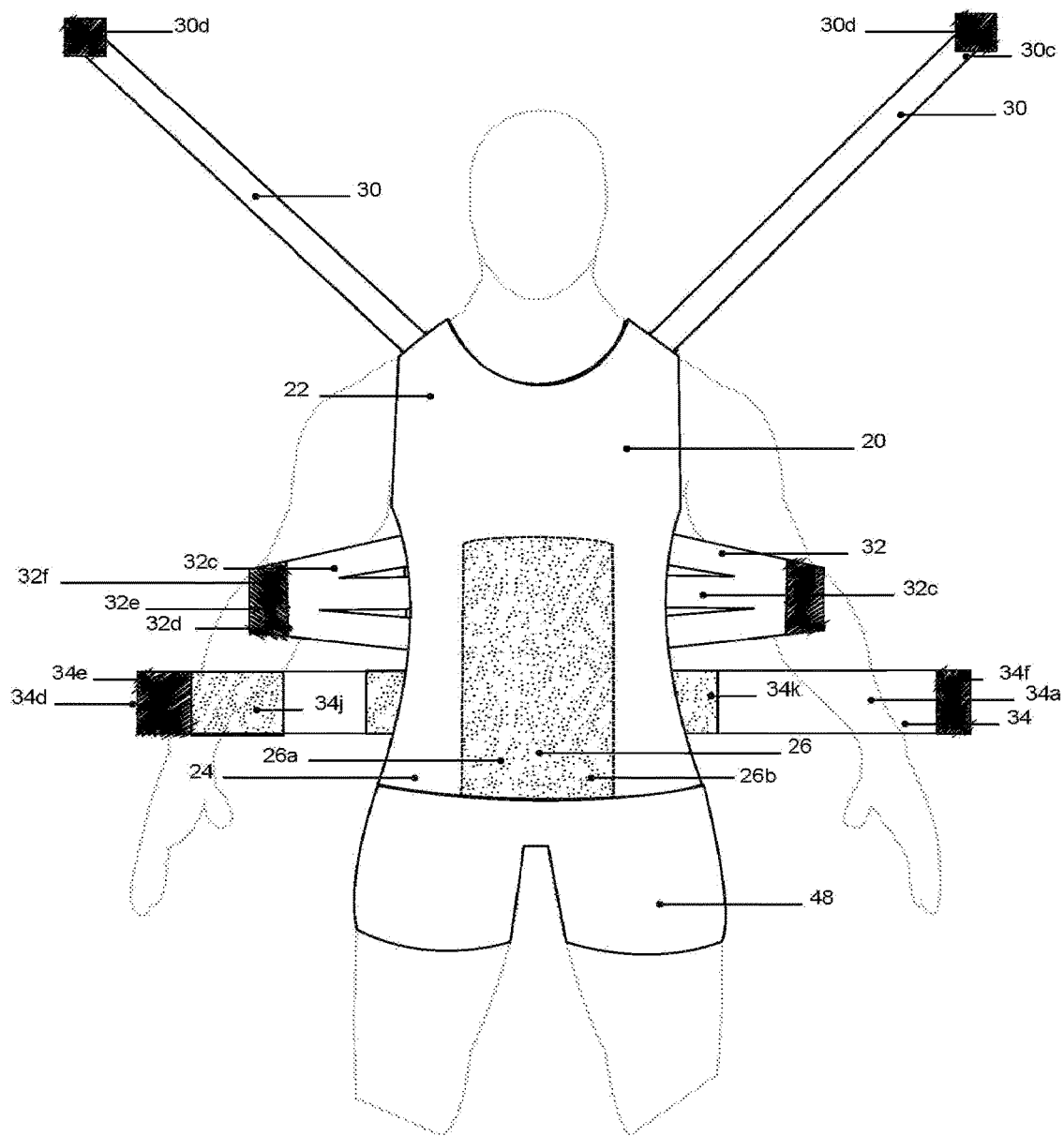
FIG. 7 front view of the postural corrective garment of an exemplary embodiment where all detachable components are disengaged.
Figure 23:
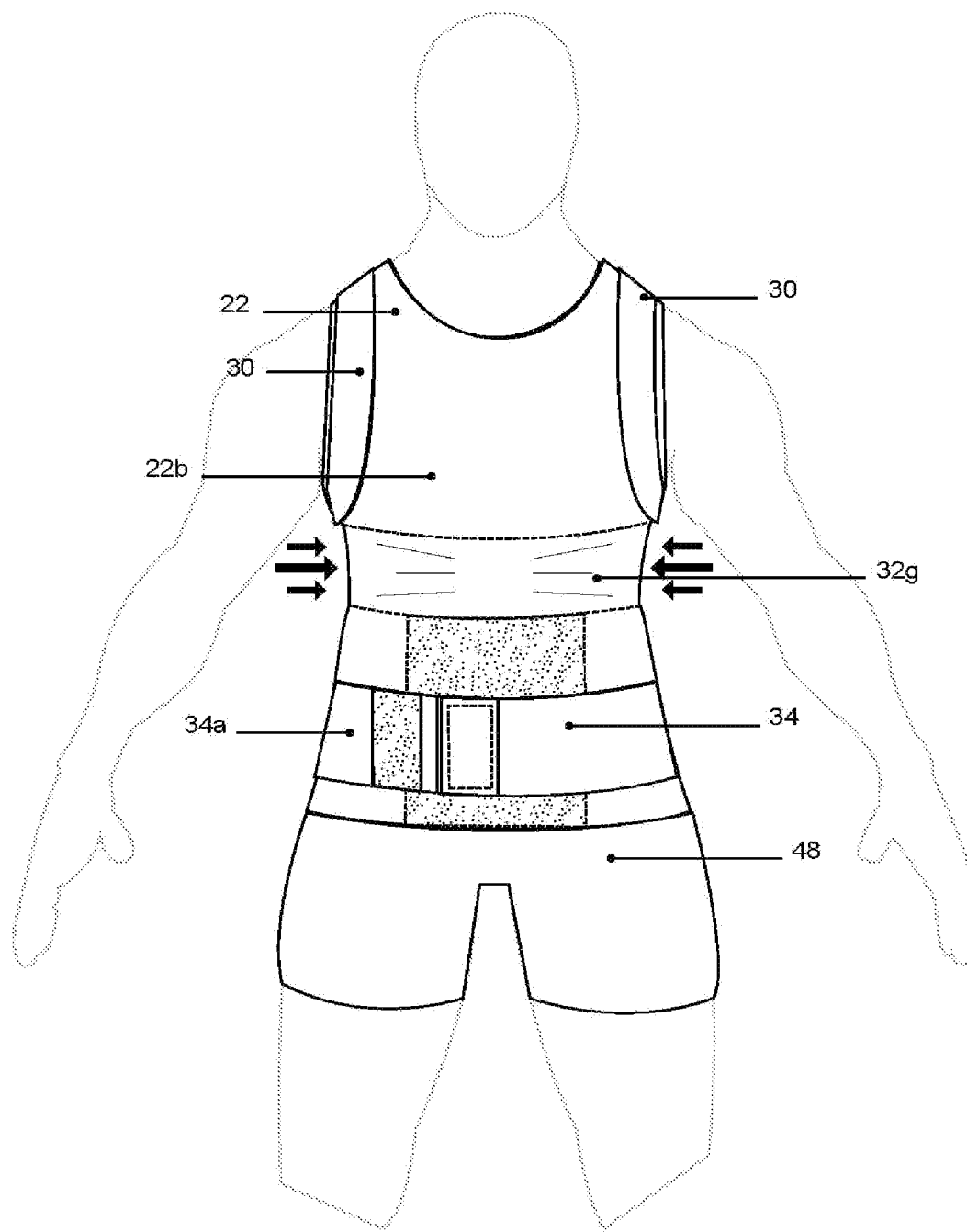
FIG. 23 is a front view of an alternative embodiment of the abdominal engagement system where it is comprised of a single piece of elastomeric material.

Now referring generally to FIGS. 1-8A, the shirt portion 22 further includes an abdominal engagement system 32 including two straps 32c, preferably elastic, each strap 32c having an end 32a that is fixedly attached to the back 22a of the shirt portion 22. Any method, such as sewing, is acceptable to fixedly attach abdominal engagement system 32 to back 22a of the shirt portion 22. Alternatively, one single strap 32c can be used. The abdominal engagement system 32 wraps around the wearer's abdomen from the back panel 28 to the front panel 26 where it is releasably attached to the loops 26a of the front panel by hooks 32f attached to a portion 32e of the free ends 32d of the straps 32c. FIGS. 2, 3 and 4 show the abdominal engagement system 32 of an exemplary embodiment engaged with the front panel 26 of the shirt portion 22, while FIG. 7 shows the abdominal engagement system 32 disengaged from the front panel 26. The straps 32c compress the abdominal muscles of the wearer promoting abdominal bracing for super-stiffness of abdominal wall musculature leading to stabilization of the spine. In an alternative embodiment, illustrated in FIG. 23, the abdominal engagement system 32 may consist of a single piece of elastomeric material 32g, which could be made from elastic or any compressive fabric, which surrounds the mid-section of the user and is not releasably attached to the front panel. This material may have some other method of tightening or loosening, such as a method similar to tightening a corset, to allow donning and doffing of the garment. Or, if made from a single piece of non-adjustable continuous material, strap 32C can be capable of being stretched when pulled over the user and capable of contracting when situated over the mid-section to apply compression.

Figure 15:
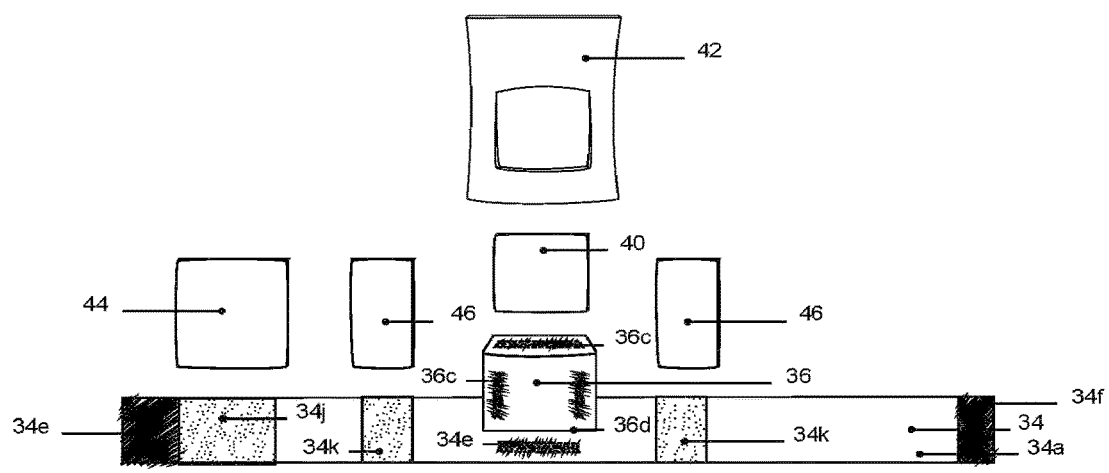
FIG. 15 is an inner surface view of all removable components disengaged, including attachable belt, panels, and inserts.
Figure 16:
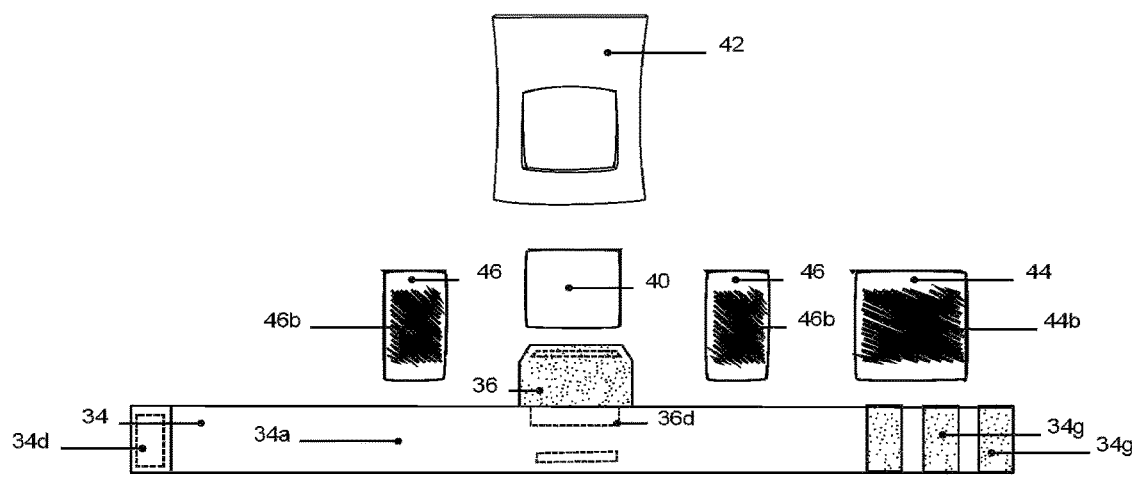
FIG. 16 is an outer surface view of all removable components disengaged, including attachable belt, panels, and inserts.
Figure 17:
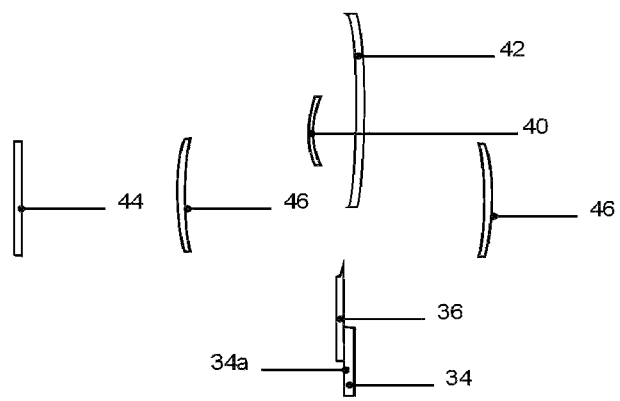
FIG. 17 are profile views of all removable components disengaged, including attachable belt, panels, and inserts.
Figure 18:
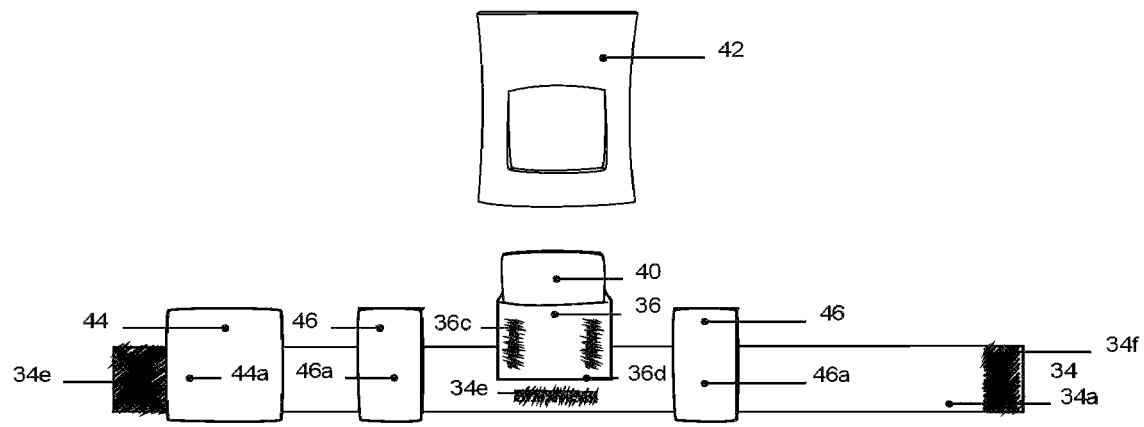
FIG. 18 is an inner surface view of all removable components, including attachable belt, panels, and inserts, where the anterior support panel and lateral counterpoise panels are connected to the lumbar stabilization belt, and the posterior positioning panel is partially inserted into the external pocket.

Now turning to FIGS. 1 and 15-18 that illustrate the shirt portion 22 that also includes an external pocket 36, which attaches to the outer surface of the back panel 28 that receives a posterior positioning panel 40. The external pocket can be fixedly attached or releasably attached through a hook and loop or other adjustable fastening system. The positioning panel 40 is preferably made of a thermoplastic material that is custom molded to the wearer's back when the spine is in the neutral position, although other materials can be used as well. The posterior positioning panel 40 creates a constant awareness of the proper positioning of the wearer's neutral spine. The posterior positioning panel 40 may also be directly fixedly attached or releasably attached to the back panel 28 of the shirt portion 22 through a hook and loop or other adjustable fastening system without the use of the external pocket 36. FIG. 1 shows the location of the external pocket 36 for the posterior positioning panel 40 on the back panel 28 in an exemplary embodiment. FIGS. 15-17 show inward facing, outward facing, and profile views, respectively, of an exemplary embodiment of the posterior positioning panel 40, posterior extension frame 42, anterior support panel 44, and lateral counterpoise panels 46.

Figure 19:
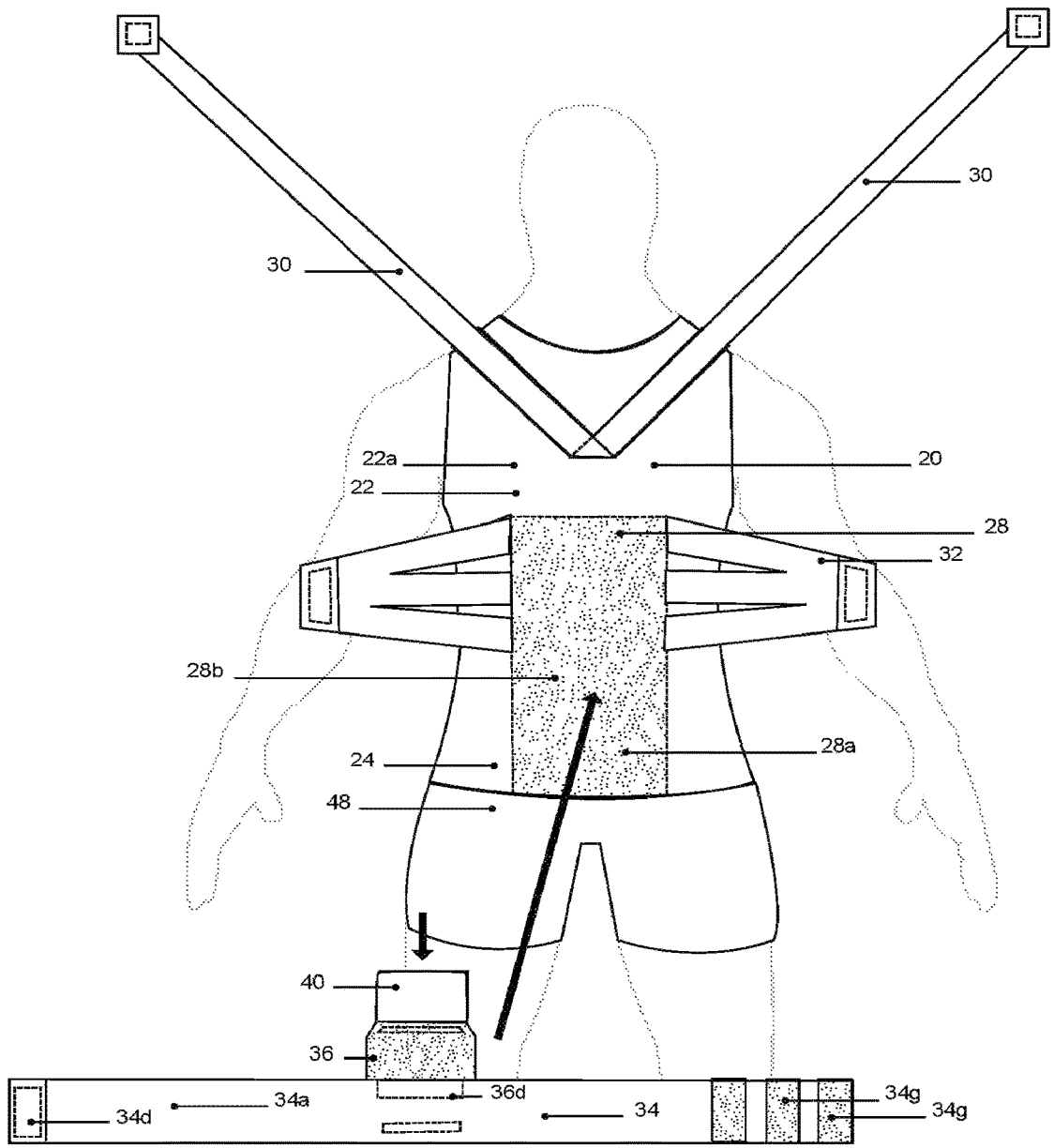
FIG. 19 is a back view of the postural corrective device demonstrating the connection mechanism of the posterior positioning panel received by an external pocket, that is attached to the lumbar stabilization belt, and then attached to the back panel.
Figure 20:
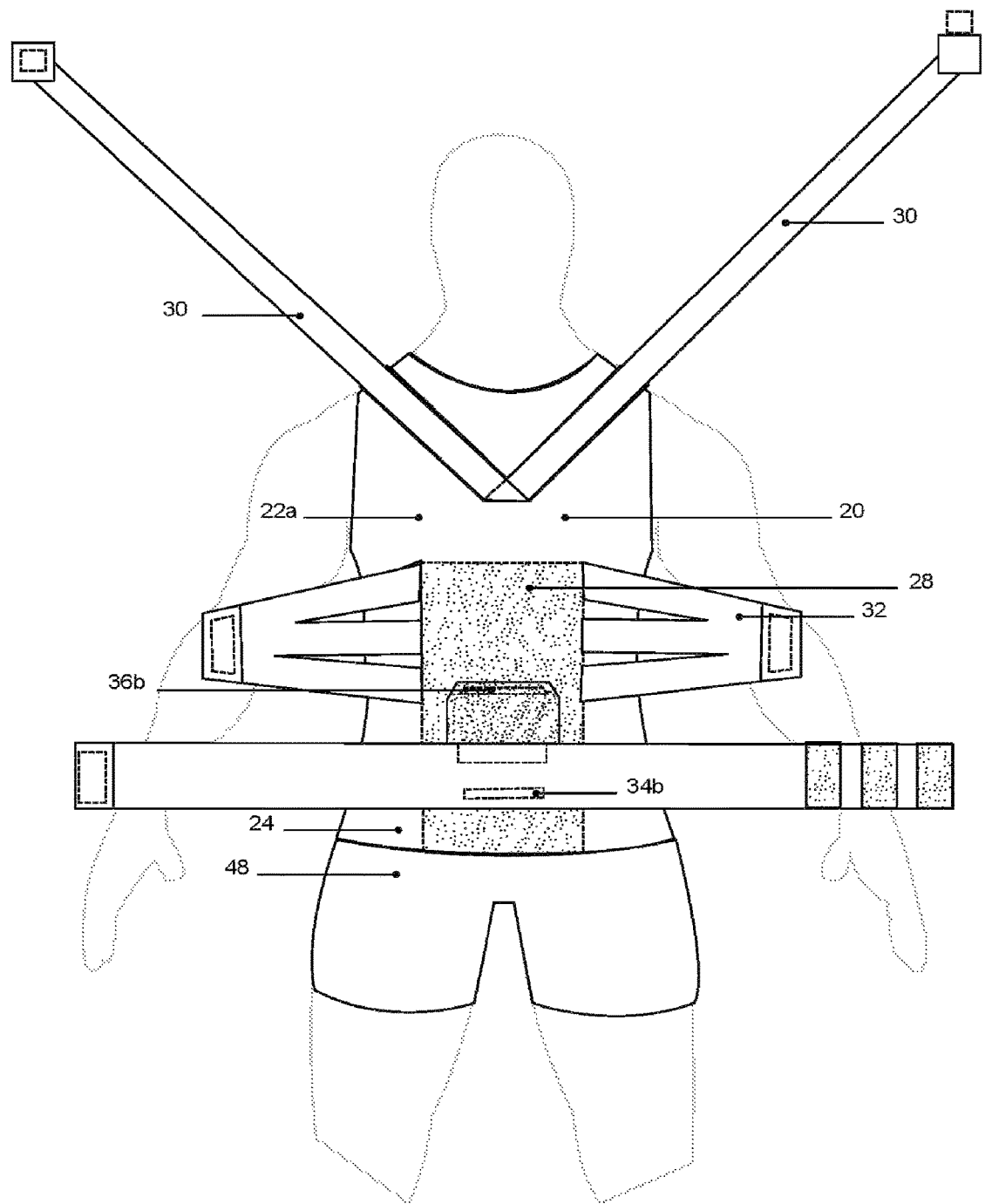
FIG. 20 is a back view of the postural corrective device demonstrating the posterior positioning panel received by an external pocket, that is attached to the lumbar stabilization belt, and attached to the back panel.
Figure 26:
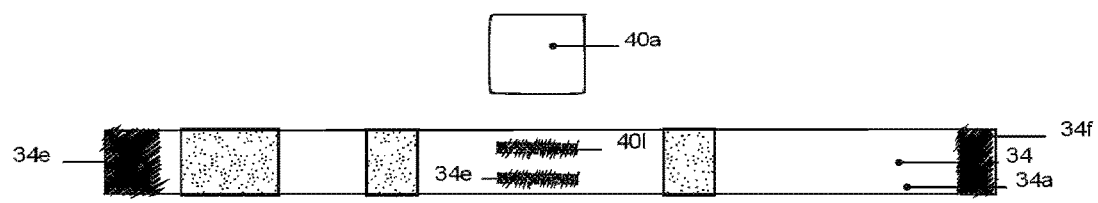
FIG. 26 is an inner surface view of an alternate embodiment of the posterior positioning panel that can be directly attached to the lumbar stabilization belt through a hook and loop attachment system, without being received by an external pocket.
Figure 27:
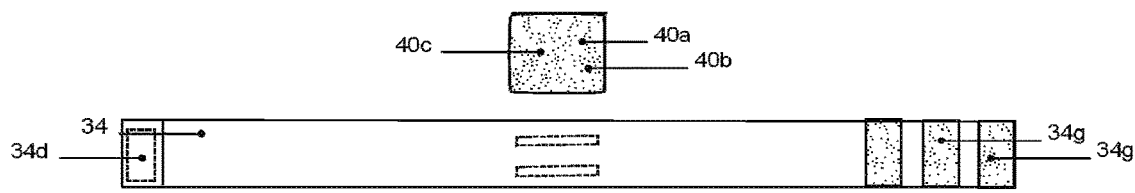
FIG. 27 is an outer surface view of an alternate embodiment of the posterior positioning panel that can be directly attached to the lumbar stabilization belt through a hook and loop attachment system, without being received by an external pocket.
Figure 28:
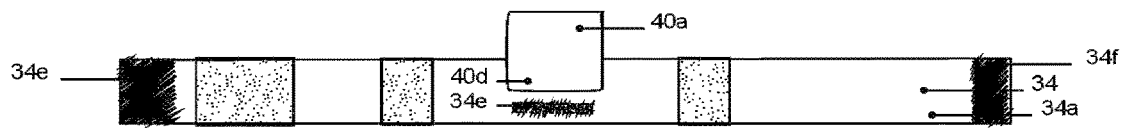
FIG. 28 is an inner surface view of an alternate embodiment of the posterior positioning panel that can be directly attached to the lumbar stabilization belt through a hook and loop attachment system, without being received by an external pocket.

Now turning to FIGS. 1-7, 9-20, 23-24, and 26-28. illustrating the shirt portion 22 that can include a lumbar stabilization belt 34 including a thick band 34a, preferably elastic, encompassing the lumbosacral region that is attached to the back panel 28 of the shirt portion 22 (see FIG. 1) by any suitable attachment mechanism (see FIG. 19). The lumbar stabilization belt 34 is also in contact with the posterior positioning panel 40 either indirectly through an attachment to the external pocket 36 which receives the posterior positioning panel 40 as seen in FIGS. 16-19, or directly attached to the posterior positioning panel 40 as seen in FIGS. 26-28. The lumbar belt may be fixedly or releasably attached to the external pocket 36 or posterior positioning panel 40 through any acceptable mechanism which may include sewing or a hook and loop attachment system. FIG. 19 shows an embodiment of the lumbar stabilization belt 34 which attaches to the back panel 28 of the shirt portion 22 and external pocket 36 with the posterior positioning panel 40 partially inserted. The lumbar stabilization belt 34 includes two free ends 34d that wrap around the shirt portion 22 to the front panel 26 where it releasably attaches to the loops 26a of the front panel 26 by hooks of a hook and loop fastener system 34e attached to a portion of each free end 34d of the lumbar stabilization belt 34, or attaches to the opposite free end 34d of the lumbar stabilization belt 34. FIGS. 2-4 show front, right and left side views, respectively, of a lumbar stabilization belt 34 of an exemplary embodiment that has been wrapped around the wearer and releasably attached to the opposite free end 34d of the lumbar stabilization belt 34 through the hook and loop fastener system 34c. FIG. 7 shows a front view of an exemplary embodiment of the postural corrective device or present invention 20 with the lumbar stabilization belt 34 not engaged with the front panel 26. The lumbar stabilization belt 34 further is a corrective aspect that serves to mitigate wearer pain through the compressive force of the belt relieving pressure from inter-vertebral discs of the lumbosacral region.

Figure 9:
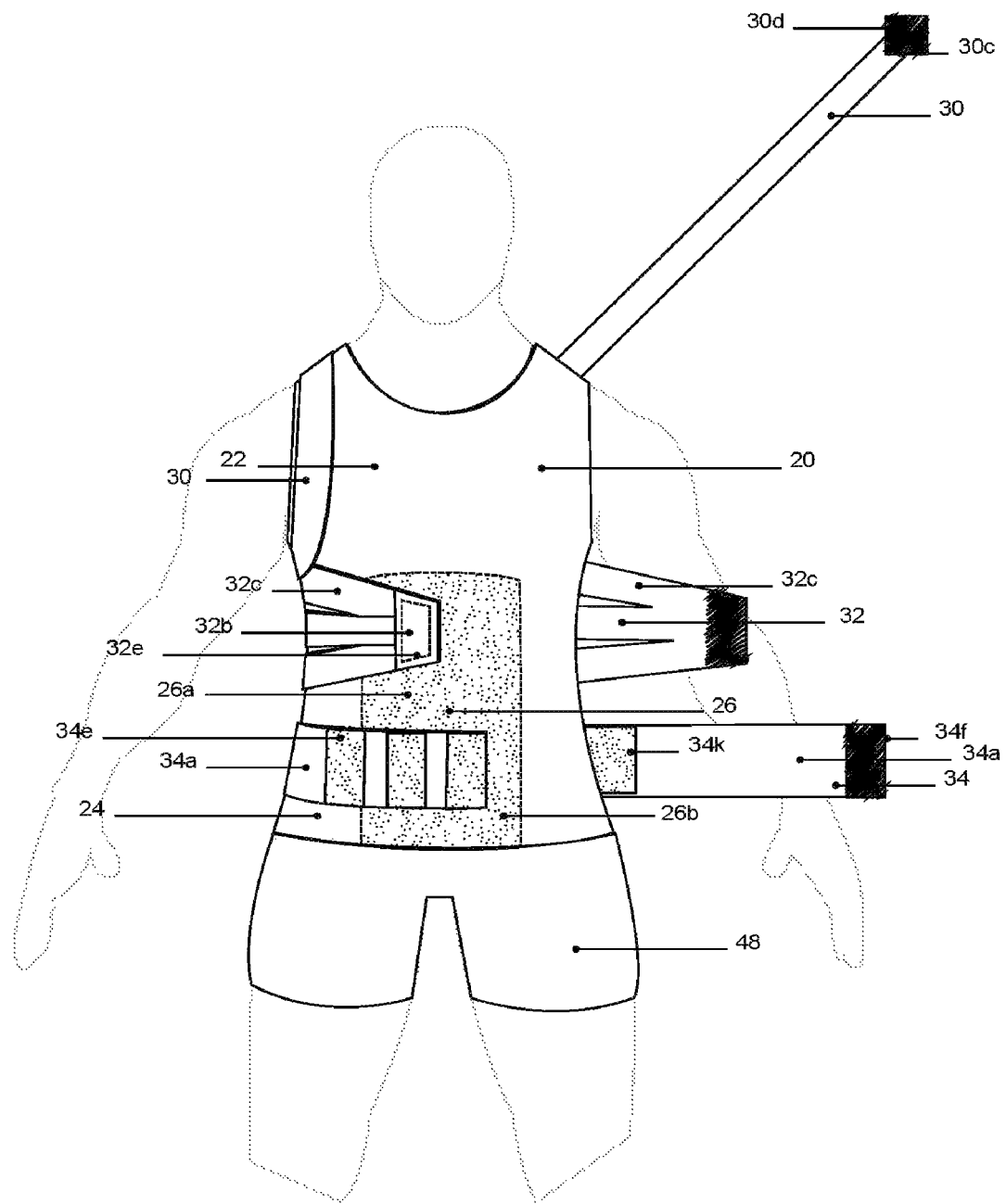
FIG. 9 is a front view of the postural corrective garment of an exemplary embodiment with the left side of the scapular correction straps, abdominal engagement system and lumbar stabilization belt disengaged from the front panel of the garment.
Figure 10:
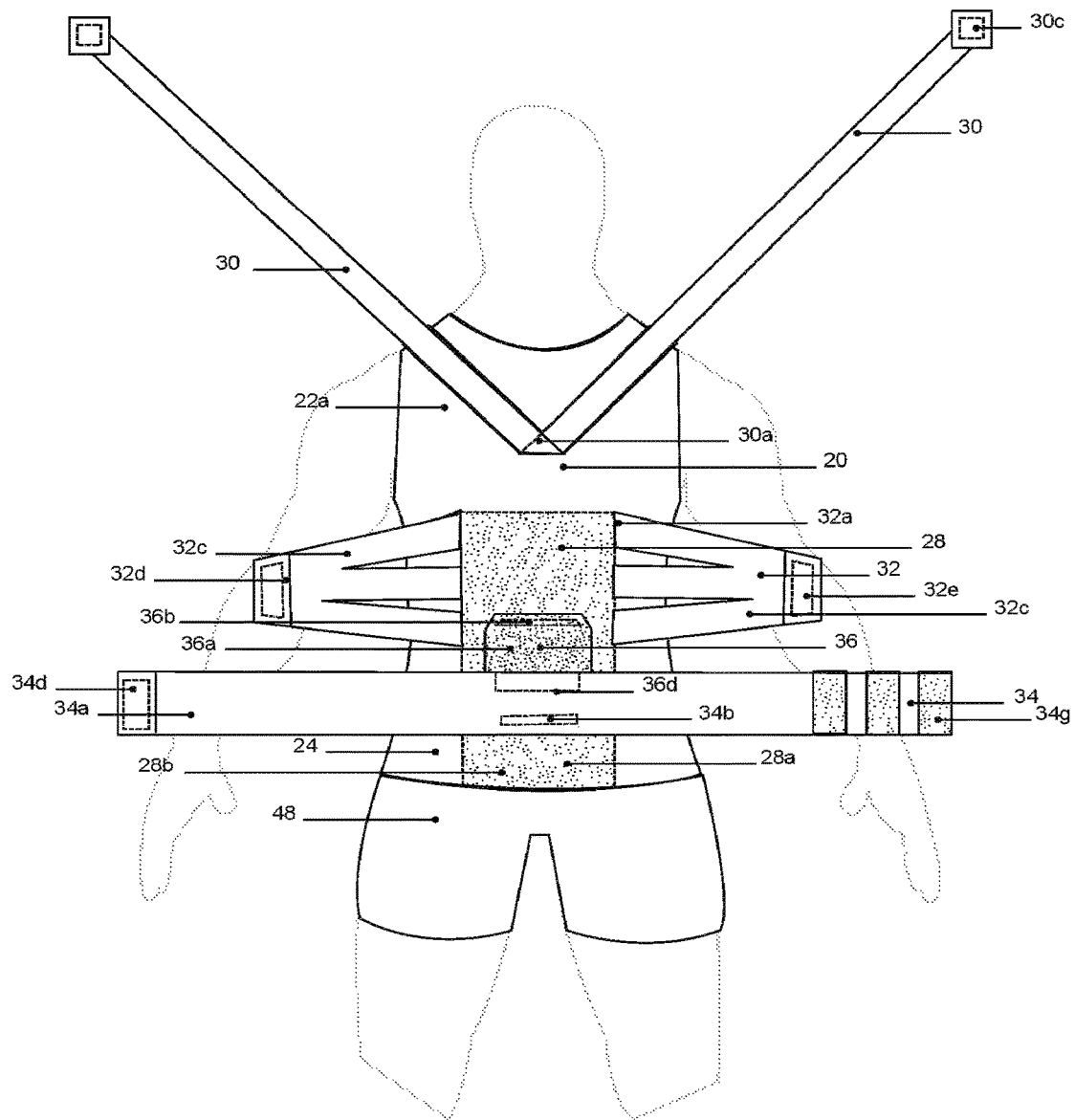
FIG. 10 is a back view of the postural corrective garment of an exemplary embodiment where all detachable components are disengaged.

Now turning to FIGS. 1-5, 7, 8A, 9-14, 19-20, and 23-25b illustrates that the shirt portion 22 can also include scapular correction straps 30, a pair of adjustable elastomeric straps fixedly attached at point 30a (see FIGS. 1, 8A, 10, and 12) to the back side 22a of the shirt portion 22 between the wearer's scapulae. These adjustable straps 30 further wrap around the front of the wearer's shoulder and under the armpit to where the strap free ends 30c are releasably attached at points 30b to the back panel 28 of shirt portion 22 in the mid to lower back region (see FIGS. 1 and 12). Preferably, the free end 30c of each strap 30 has a portion of hooks of a hook and loop fastener system 30d (see FIGS. 7, and 9) that engage the loops 28a on the back panel 28 integrated into the shirt portion 22. Again, other fastening systems may be suitable. Now turning to FIGS. 1-4 that show back, front, right and left side views, respectively, of the postural corrective device 20 of an exemplary embodiment and illustrate the positioning of the scapular correction straps 30 on the shirt portion 22 with the free ends 30c of the straps 30 releasably attached to the shirt portion 22. Now turning to FIG. 5 that shows a top view of the postural corrective garment 20 of an exemplary embodiment illustrating the strap 30 positioning over the top of the shirt portion 22 when the free ends 30c of the straps 30 are attached to the shirt portion 22. FIG. 9 shows a front view of the postural corrective garment 20 of an exemplary embodiment with scapular correction straps 30, abdominal engagement system 32, and lumbar stabilization belt 34 attached to the shirt portion 22 on the right side, while disengaged on the left side. The scapular correction straps 30 pull the shoulders back, training proper posture and preventing kyphosis.

Figure 11:
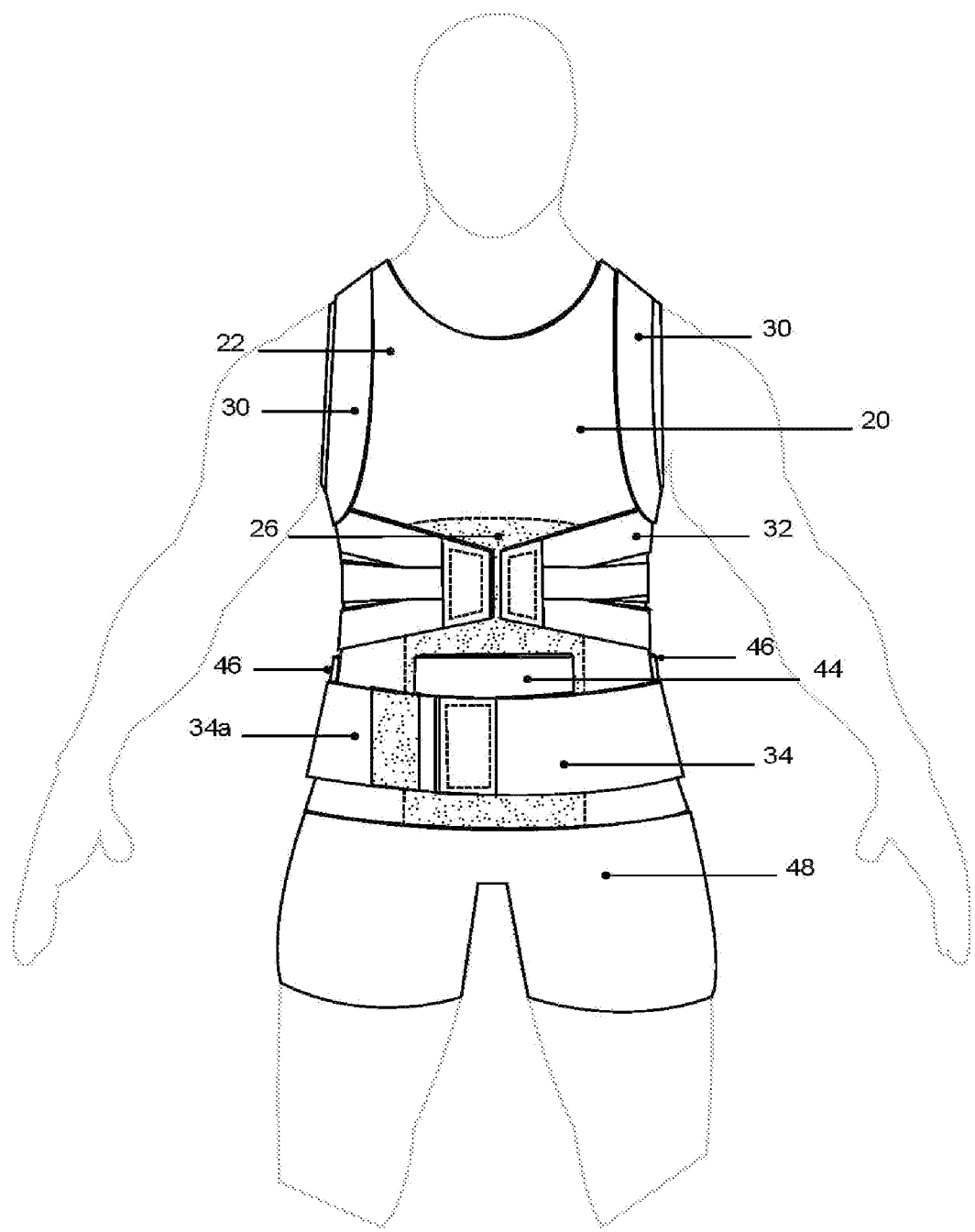
FIG. 11 is a front view of the postural corrective garment of another embodiment where all detachable and removable optional components are included.
Figure 12:
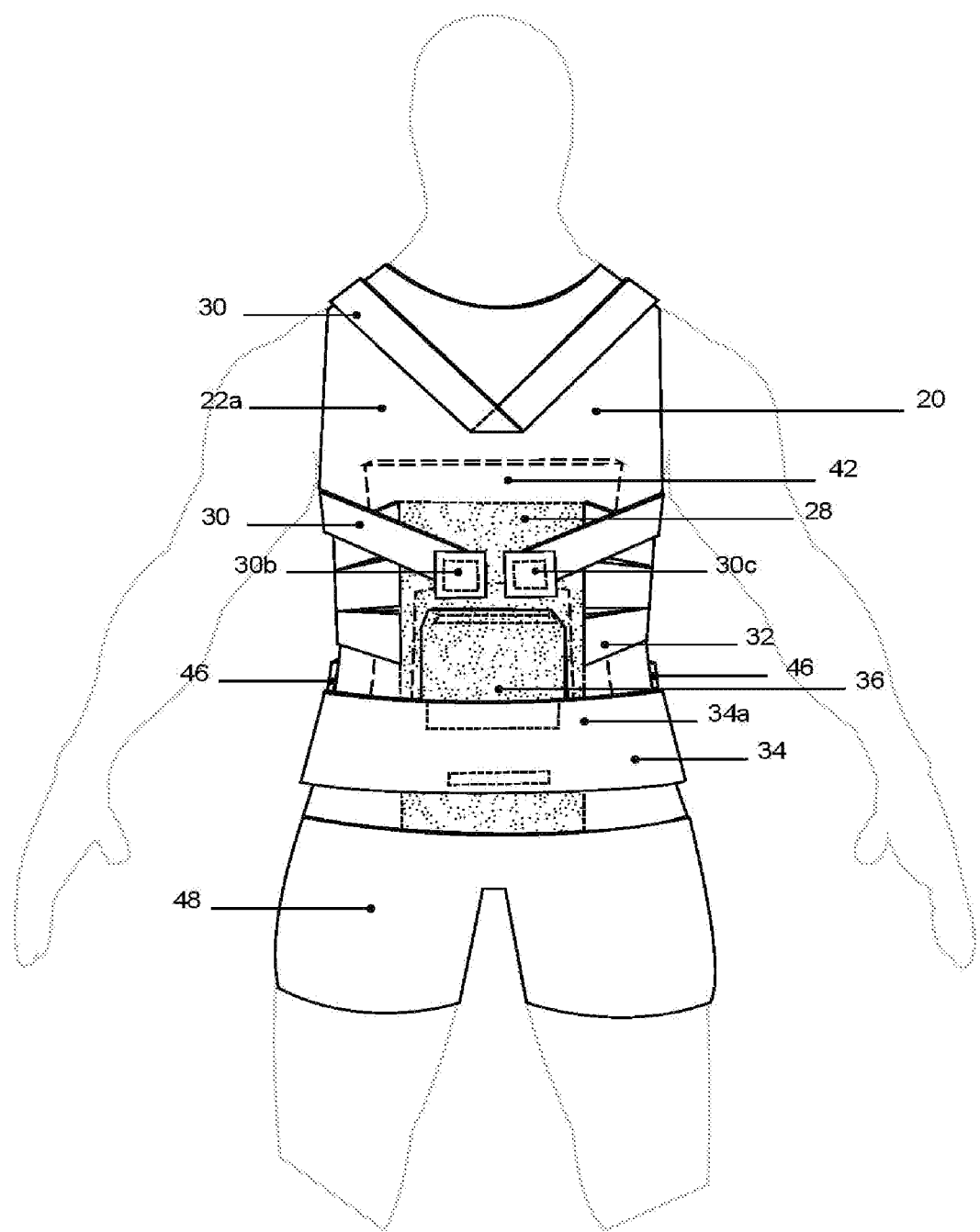
FIG. 12 is a back view of the postural corrective garment of another embodiment where all detachable and removable optional components are included.
Figure 21:
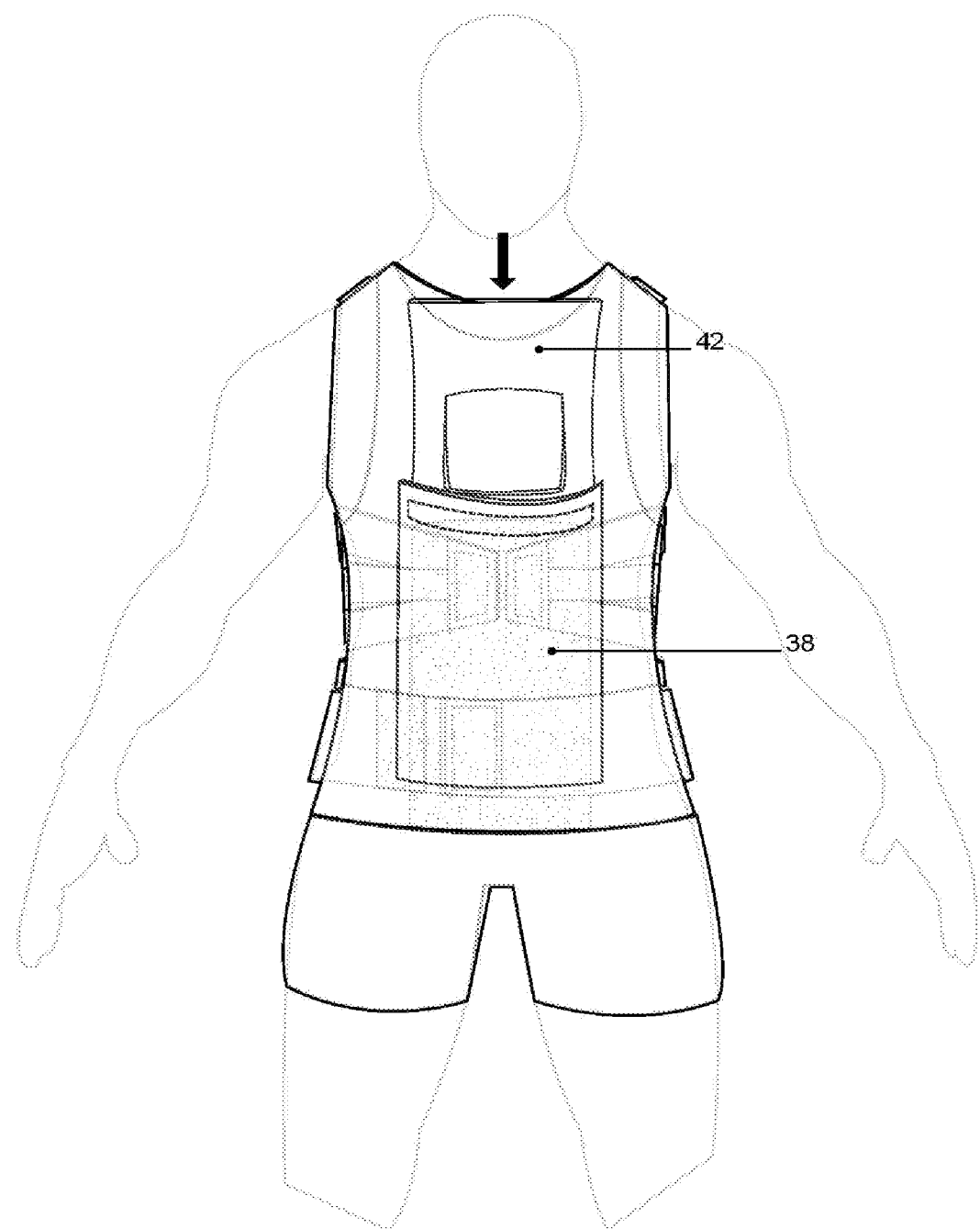
FIG. 21 is a back inner surface view of the postural corrective device showing a possible mechanism of attachment of the posterior extension panel received by an internal pocket.
Figure 22:
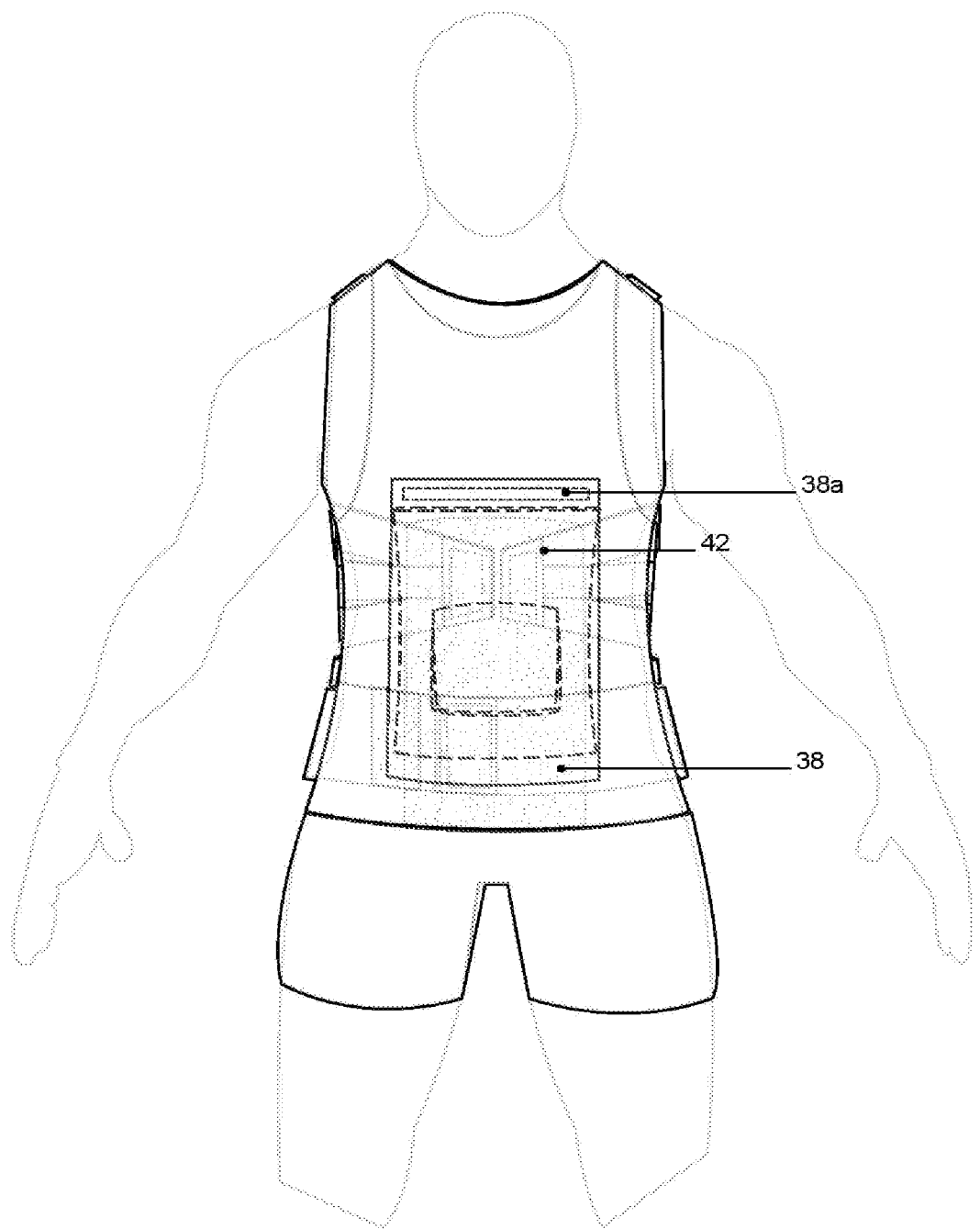
FIG. 22 is a back inner surface view of the postural corrective device showing the attachment of the posterior extension panel received by an internal pocket.

The postural corrective device 20 can also contain additional removable panels and frames. FIG. 12 shows the posterior view of the alternate embodiment with the posterior extension frame 42 which covers the wearer's back from the t9 vertebra to the sacrum, with the center of the frame 42 cut out. This frame 42 is in contact with the back of the shirt portion 22a and attached by a releasable mechanism such as a hook and loop attachment system or held inside of an internal pocket 38 connected to back of the shirt portion 22a (FIG. 21). The frame 42 is made from a semi rigid thermoplastic material which can be formed at low temperatures. FIGS. 11, 13, and 14 show front and side views of this alternate embodiment, respectively, which includes an anterior support panel 44 and lateral counterpoise panels 46 on each the right and left side of the garment. These panels 44, 46 are releasably attached to the lumbar stabilization belt 34 though a hook and loop system. These panels 44, 46 are made from semi rigid thermoplastic material which can be formed at relatively low temperatures.

The advantages of the postural corrective device 20 also include its low-profile and adjustable design. The postural corrective device 20 is preferably composed of breathable material which can consist of a blend of polyester, nylon, elastane or other materials to form the shirt portion 22 which may additionally include a shorts portion 48 that is connectable to form a body suit 24. The postural corrective device 20 can be worn subtly and comfortably underneath everyday clothes, allowing continuous treatment without interfering with daily life. Patient compliance is essential to effective treatment, and the present invention encourages patient compliance and long term benefit by training self-corrective habits through proprioceptive feedback, offering gentle reminders to create awareness of what the patient's body is doing.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A postural corrective device adapted for interaction with or support to the abdomen, abdominal muscles, spine, shoulders, scapulae, armpits and lumbar and lumbosacral regions of the back of a wearer of the postural corrective device, the postural corrective device comprising:
   a shirt portion comprising a front side and a back side, wherein the front side and the back side each comprise an inner surface and an outer surface;
   a front panel of non-stretch material comprising a plurality of loops of a first hook and loop fastener system on the outer surface of the front side of the shirt portion;
   a back panel of non-stretch material comprising a plurality of loops of a second hook and loop fastener system on the outer surface of the back side of the shirt portion;
   an abdominal engagement system comprising two straps, wherein each strap comprises an attached terminal end fixedly attached to the back side of the shirt portion, wherein each strap further comprises a free end, wherein each free end of the each strap comprises a plurality of hooks of a third hook and loop fastener system, wherein the two straps are configured to extend around the upper abdomen of the wearer and each free end is configured to releasably attach a portion of the plurality of hooks of the third hook and loop fastener system to a portion of the plurality of loops of the first hook and loop fastener system of the front panel, and wherein the two straps of the abdominal engagement system are configured to work in conjunction with the front panel to compress the abdominal muscles of the wearer of the postural corrective device and thereby promote abdominal bracing for super-stiffness of the abdominal wall musculature and stabilization of the spine of the wearer;
   a pair of adjustable scapular correction straps separate and distinct from the two straps of the abdominal engagement system and the pair of adjustable scapular corrections straps comprising two attached ends adapted to fixedly attach to the back side of the shirt portion between the scapulae of the wearer, wherein each strap of the pair of adjustable scapular correction straps further comprises a free end, wherein each free end of the pair of adjustable scapular correction straps comprises a plurality of hooks of a fourth hook and loop fastener system, wherein each strap of the pair of adjustable scapular correction straps is configured to extend over the shoulder of the wearer, around a front of the shoulder of the wearer, and under the armpit of the wearer, wherein a portion of the plurality of hooks of the fourth hook and loop fastener system for each free end is configured to releasably attach to a portion of the plurality of loops of the second hook and loop fastener system on the back panel said adjustable scapular correction straps adapted to pull the shoulders of the wearer back and thereby train proper posture; and
   a posterior positioning panel adapted to contact the outer surface of the back side of the shirt portion in the lumbar region of the back of the wearer and configured to provide awareness of proper spine positioning for the wearer of the postural corrective device.

2. The postural corrective device as in claim 1, further comprising a lumbar stabilization belt configured to attach to the outer surface of the back side of the shirt portion in the lumbosacral region of the back of the wearer and the lower abdominal region of the front of the wearer, wherein the lumbar stabilization belt comprises two free ends, wherein each free end comprises a plurality of hooks of a fifth hook and loop fastener system, wherein each free end of the lumbar stabilization belt configured to extend around an abdomen of the wearer and releasably engaging a portion of the plurality of hooks of the fifth hook and loop fastener system with (i) a portion of the plurality of hooks of the fifth hook and loop fastener system of the other free end of the two free ends of the lumbar stabilization belt, and (ii) a portion of the plurality of loops of the first hook and loop fastener system of the front panel.

3. The postural corrective device as in claim 2, wherein the lumbar stabilization belt is elastic.

4. The postural corrective device as in claim 2, wherein the posterior positioning panel is adapted to directly contact the outer surface of the back side of the shirt portion in the lumbar region of the back of the wearer and in contact with an inner surface of the lumbar stabilization belt.

5. The postural corrective device as in claim 1, wherein the posterior positioning panel is made of a semi-rigid thermoplastic material custom molded and adapted to conform to a contour of the back of the wearer and thereby configured to provide awareness of proper spine positioning for the wearer of the postural corrective device.

6. The postural corrective device as in claim 1, further comprising a shorts portion.

7. The postural corrective device as in claim 6, wherein the shorts portion and the shirt portion each comprise cooperating attachment devices to attach the shorts portion and the shirt portion thereto.

8. The postural corrective device as in claim 6, wherein the shorts portion and the shirt portion comprise a single piece of clothing.

9. The postural corrective device as in claim 1, wherein the two straps of the abdominal engagement system are elastic.

10. The postural corrective device as in claim 1, wherein the posterior positioning panel is received by an external pocket.

11. The postural corrective device as in claim 1, further comprising an external pocket attached to an outer surface of the back panel, wherein the external pocket is sized to receive the posterior positioning panel.

* * * * *